United States Patent
Kato (10) Patent No.: US 9,630,984 B2
(45) Date of Patent: Apr. 25, 2017

(54) COMPOUND CONTAINED IN MANUKA HONEY AND USE OF SAME

(71) Applicants: Yoji Kato, Himeji-shi, Hyogo (JP); HEALTHCARE SYSTEMS, Nagoya-shi, Aichi (JP)

(72) Inventor: Yoji Kato, Himeji (JP)

(73) Assignees: Yoji Kato, Himeji-Shi, Hyogo (JP); HEALTHCARE SYSTEMS, Nagoya-Shi, Aichi (JP)

(*) Notice: Subject to any disclaimer, the term of this patent is extended or adjusted under 35 U.S.C. 154(b) by 0 days.

(21) Appl. No.: 14/354,314

(22) PCT Filed: Oct. 15, 2012

(86) PCT No.: PCT/JP2012/076645
§ 371 (c)(1),
(2) Date: Apr. 25, 2014

(87) PCT Pub. No.: WO2013/061816
PCT Pub. Date: May 2, 2013

(65) Prior Publication Data
US 2014/0274931 A1    Sep. 18, 2014

(30) Foreign Application Priority Data
Oct. 27, 2011 (JP) .................. 2011-236137

(51) Int. Cl.

| | | |
|---|---|---|
| C07G 11/00 | (2006.01) | |
| C07H 15/00 | (2006.01) | |
| C07H 17/00 | (2006.01) | |
| A01N 43/04 | (2006.01) | |
| A61K 31/70 | (2006.01) | |
| G01N 30/00 | (2006.01) | |
| G01N 31/00 | (2006.01) | |
| G01N 33/00 | (2006.01) | |
| C07H 15/207 | (2006.01) | |
| C07H 15/203 | (2006.01) | |
| C12Q 1/28 | (2006.01) | |
| A61K 31/235 | (2006.01) | |
| A61K 31/7034 | (2006.01) | |
| C07H 1/08 | (2006.01) | |
| G01N 33/15 | (2006.01) | |
| C12Q 1/18 | (2006.01) | |

(52) U.S. Cl.
CPC ......... *C07H 15/207* (2013.01); *A61K 31/235* (2013.01); *A61K 31/7034* (2013.01); *C07H 1/08* (2013.01); *C07H 15/203* (2013.01); *C12Q 1/18* (2013.01); *C12Q 1/28* (2013.01); *G01N 33/15* (2013.01)

(58) Field of Classification Search
CPC ...... C07H 15/203; C07H 1/08; C07H 15/207; C12Q 1/18; C12Q 1/28; G01N 33/15; A61K 31/7034; A61K 31/235
See application file for complete search history.

(56) References Cited

U.S. PATENT DOCUMENTS 8,679,527 B2 * 3/2014 Keiji .................. A23B 7/154
                                                        424/447
2011/0263528 A1   10/2011 Keiji et al.

FOREIGN PATENT DOCUMENTS

| JP | A-2006-321778 | 11/2006 |
|---|---|---|
| JP | A-2007-277210 | 10/2007 |
| JP | A-2008-501361 | 1/2008 |
| JP | A-2010-505817 | 2/2010 |
| JP | A-2010-95454 | 4/2010 |
| WO | WO 2005/120250 A1 | 12/2005 |
| WO | WO 2008/041218 A1 | 4/2008 |

OTHER PUBLICATIONS

Ali et al., "Phenyl Alcohol and Phenolic Glysosides From the Stem Bark of *Morus alba* L," The Natural Products Journal, 2(4), 259-262 (2012); only CAPLUS Abstract supplied.*
Kato et al., "Inhibition of Myeloperoxidase-Catalyzed Tyrosylation by Phenolic Antioxidants in vitro," Biosci. Biotechnol. Biochem, vol. 67, No. 5, pp. 1136-1139, 2003.
Apr. 13, 2015 Extended European Search Report issued in European Application No. 12844559.0.

(Continued)

*Primary Examiner* — Lawrence E Crane
(74) *Attorney, Agent, or Firm* — Oliff PLC (57) ABSTRACT

The present description discloses a novel biologically active ingredient of manuka honey. Specially, the present description discloses a compound represented by the following formula. In this formula, each of $R_1$, $R_2$ and $R_3$ independently represents a hydrogen atom or optionally substituted $C_{1-4}$ alkyl group, m represents an integer from 1 to 3, each of $R_{4-m}$, $R_{5-m}$ and $R_{6-m}$ independently represents a hydrogen atom or optionally substituted $C_{1-4}$ alkyl group, and each of $R_7$, $R_8$, $R_9$ and $R_{10}$ independently represents a hydrogen atom or optionally substituted $C_{1-4}$ alkyl group.

[C7]

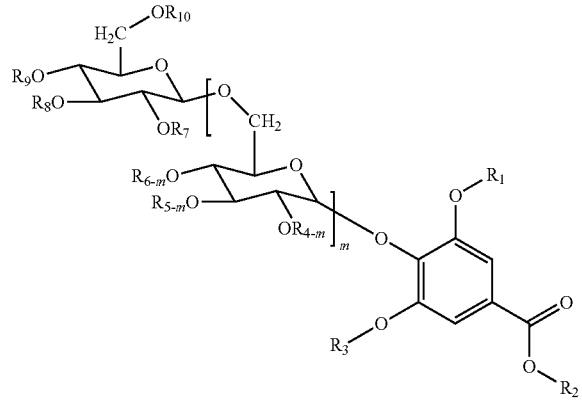

11 Claims, 9 Drawing Sheets

(56) References Cited

OTHER PUBLICATIONS

Inoue et al., "Identification of Phenolic Compound in Manuka Honey as Specific Superoxide Anion Radical Scavenger Using Electron Spin Resonance (ESR) and Liquid Chromatography with Coulometric Array Detection," *Journal of the Science of Food and Agriculture*, 2005, vol. 85, pp. 872-878.

Adams et al., "Isolation by HPLC and Characterisation of the Bioactive Fraction of New Zealand Manuka (*Leptospermum scoparium*) Honey," *Carbohydrate Research*, 2008, vol. pp. 651-659.

Mavric et al., "Identification and Quantification of Methylglyoxal as the Dominant Anibacterial Constituent of Manuka (*Leptospermum scoparium*) Honeys from New Zealand," *Mol. Nutr. Food Res.*, 2008, vol. 52, pp. 483-489.

Tuberoso et al., "Methyl Syringate: A Chemical Marker of Asphodel (*Asphodelus microcarpus* Salzm. Et VIv.) Monofloral Honey," *Journal Agricultural and Food Chemistry*, 2009, vol. 57, pp. 3895-3900.

Fujimatu et al., "Aromatic Compound Glucosides, Alkyl Glucoside and Glucide from the Fruit of Anise," *Phytochemistry*, 2003, vol. 63, pp. 609-616.

Ma et al., "Four New Phenolic Diglycosides from the Roots of *Illicium ogligandrum*," *Carbohydrate Research*, 2011, vol. 346, pp. 1165-1168.

Kato et al,. "Manuka Honey ni Fukumareru Enhosei Koso Myeloperoxydase Sogai Busshitsu no Tansaku," *Japan Society for Bioscience, Biotechnology, and Agrochemistry Taikai Koen Yoshishu*, 2010, vol. 2010, pp. 168.

International Search Report issued in International Patent Application No. PCT/JP2012/076645 dated Nov. 6, 2012 (with translation).

Written Opinion issued in International Patent Application No. PCT/JP2012/076645 dated Nov. 6, 2012 (with translation).

Office Action issued in Japanese Patent Application No. 2013-540730 dated Feb. 25, 2014 (with partial translation).

\* cited by examiner

NMR data (in CD$_3$OD)

| Carbon No. | $\delta_C$ (ppm) 125MHz | $\delta_H$ [ppm, multiplicity, $J$ (Hz)] 500MHz | HMBC ($\delta_H$) |
|---|---|---|---|
| 1 | 127.2 | | 7.34 |
| 2,6 | 108.3 | 7.34 (2H, s) | |
| 3,5 | 154.3 | | 7.34; 3.887 |
| 4 | 140 | | 7.34; 5.07 |
| 3,5-OCH$_3$ | 57 | 3.887 (6H, s) | |
| <u>C</u>OOCH$_3$ | 168.1 | | 7.34; 3.885 |
| COO<u>C</u>H$_3$ | 52.8 | 3.885 (3H, s) | |
| 1' | 104.1 | 5.07 (d, 7.8) | 3.5 |
| 2' | 75.6 | 3.50 (dd, 7.8, 9.3) | 3.4 |
| 3' | 77.7 | 3.40 (m) | 5.07; 3.50 |
| 4' | 71.3 | 3.40 (m) | 4.01; 3.40 |
| 5' | 78 | 3.40 (m) | 5.07; 4.01; 3.77; 3.40 |
| 6' | 69.1 | 3.77 (dd, 4.9, 12.0)<br>4.01 (brd, 12.0) | 4.20; 3.40 |
| 1'' | 104.3 | 4.20 (d, 7.8) | 4.01; 3.77; 3.10 |
| 2'' | 75.1 | 3.10 (dd, 7.8, 9.3) | 3.2 |
| 3'' | 77.8 | 3.20 (m) | 4.20; 3.10 |
| 4'' | 71.5 | 3.20 (m) | 3.80; 3.60; 3.20; 3.05 |
| 5'' | 77.8 | 3.05 (ddd, 2.2, 5.9, 9.0) | 4.20; 3.60; 3.20 |
| 6'' | 62.7 | 3.60 (dd, 5.9, 12.0)<br>3.80 (dd, 2.2, 12.0) | 3.2 |

Key HMBC correlations

MSYR

MGO

Fig. 9

COMPOUND CONTAINED IN MANUKA HONEY AND USE OF SAME

TECHNICAL FIELD

The present application relates to a novel compound contained in manuka honey, and to a use therefor.

BACKGROUND

Manuka honey is a honey unique to New Zealand, derived from the nectar of the flowers of manuka (*Leptospermum scoparium*), which grows only in New Zealand, and is known to have strong antibacterial activity and other physiological functions. However, a kind of manuka honey (jelly bush honey) is also collected from a manuka relative (*Leptospermum polygalifolium*) growing in Australia.

With its strong antibacterial activity, it is thought that manuka honey may be able to eliminate *Helicobacter pylori*, a cause of stomach cancer. Physiological activities including this antibacterial activity are thought to vary considerably among different manuka honeys.

A "Unique Manuka Factor" (UMF) based on antibacterial activity converted to phenol activity is used as one index of the antibacterial activity and other bioactivity of manuka honey. It has been reported (Non Patent Literature 1,2) that an antibacterial constituent of manuka honey is an aldehyde called methylglyoxal (MGO) (see FIG. 9). Based on this report, the amount of MGO is sometimes used as an index of the bioactivity of manuka honey.

Manuka honey has also been reported to contain methyl syringate (MSYR) (shown below), and to have active enzyme elimination ability (Non Patent Literature 3) (see FIG. 9). Apart from manuka honey, this methyl syringate is also found in large quantities in asphodel honey obtained in Sardinia, Italy (Non Patent Literature 4). In addition, a glycoside of one sugar bound to methyl syringate has been isolated and identified from aniseed (Non Patent Literature 5).

CITATION LIST

Non Patent Literature

[Non Patent Literature 1] *Isolation by HPLC and characterisation of the bioactive fraction of New Zealand manuka (Leptospermum scoparium) honey.* Adams C J, Boult C H, Deadman B J, Farr J M, Grainger M N, Manley-Harris M Snow M J. *Carbohydrate Res.* 2008; 343(4): 651-659.

[Non Patent Literature 2] *Identification and quantification of methylglyoxal as the dominant antibacterial constituent of Manuka (Leptospermum scoparium) honeys from New Zealand.* Mavric E, Wittmann S, Barth G, Henle T, *Mol Nutr Food Res.* 2008; 52(4): 483-489.

[Non Patent Literature 3] *Identification of phenolic compound in manuka honey as specific superoxide anion radical scavenger using electron spin resonance (ESR) and liquid chromatography with coulometric array detection.* Koichi Inoue, Shinho Murayama, Fumie Seshimo, Kazue Takeba, Yoshihiro Yoshimura, and Hiroyuki Nakazawa. *J. Sci. Food Agric.* 85, 872-878, 2005.

[Non Patent Literature 4] *Methyl syringate: a chemical marker of asphodel (Asphodelus microcarpus Salzm. Et Viv.) monofloral honey.* Tuberoso C I, Bifulco E, Jerković I, Caboni P, Cobras P, Floris I. *J Agric Food Chem.* 2009, 57(9): 3895-3900.

[Non Patent Literature 5] *Aromatic compound glucosides, alkyl glucoside and glucide from the fruit of anise.* Fujimoto E, Ishikawa T, Kitajima J. *Phytochemistry.* 2003, 63(5): 609-616.

SUMMARY

Technical Problem

However, because UMF evaluation requires measuring antibacterial activity, it could be complicated and time-consuming. With MGO measurement, on the other hand, rapid evaluation is also difficult because the MGO is converted to a quinoxaline before being measured by high-performance liquid chromatography (HPLC) and the like.

Manuka honey also thought to have a variety of other effects apart from antibacterial activity. Although the MGO and MSYR described above are known as active constituents, other active constituents may also be present. In that case, those compounds could serve as more effective indexes of the antibacterial activity and other bioactivity of manuka honey.

It is therefore an object of this Description to discover an effective bioactive constituent of manuka honey.

Solution to Problem

The inventors focused on screening for novel active constituents of manuka honey using a myeloperoxidase (MPO) inhibition activity evaluation system based on anti-inflammatory activity. As a result of screening, the inventors discovered a compound exhibiting strong MPO inhibition activity, and identified this compound as methyl-4-O-[β-D-glucopyranosyl-(1→6)-β-D-glucopyranosyl]-3,5-dimethoxybenzoate (MGGD), which is a glycoside of MSYR and the disaccharide gentiobiose, and was found to be a novel compound. A trisaccharide and tetrasaccharide were discovered at the same time. The inventors also discovered a correlation between MGGD and the manuka honey factor UMF, and realized that MGGD could be used as an index of antibacterial activity. The disclosures of this Description provide the following means.

(1) A compound represented by the following formula:

[C1]

(where, each of $R_1$, $R_2$ and $R_3$ independently represents a hydrogen atom or optionally substituted $C_{1-4}$ alkyl group, m represents an integer from 1 to 3, each of $R_{4\text{-}m}$, $R_{5\text{-}m}$ and $R_{6\text{-}m}$ independently represents a hydrogen atom or option- ally substituted $C_{1-4}$ alkyl group, and each of $R_7$, $R_8$, $R_9$ and $R_{10}$ independently represents a hydrogen atom or optionally substituted $C_{1-4}$ alkyl group).

(2) The compound according to (1), wherein $R_1$, $R_2$ and $R_3$ are all hydrogen atoms.

(3) The compound according to (1) or (2), wherein $R_{4-m}$, $R_{5-m}$ and $R_{6-m}$ are all hydrogen atoms.

(4) The compound according to any of (1) to (3), wherein $R_7$, $R_8$, $R_9$ and $R_{10}$ are all hydrogen atoms.

(5) The compound according to any of (1) to (4), represented by the following formula:

[C2]

(where m is an integer from 1 to 3).

(6) A myeloperoxidase activity inhibitor, comprising a compound according to any of (1) to (5) as an active ingredient.

(7) The myeloperoxidase activity inhibitor according to (6), also containing methyl syringate.

(8) A honey evaluation marker, containing the compound according to any of (1) to (5).

(9) A honey evaluation marker kit, containing the compound according to any of (1) to (8) and methyl syringate.

(10) A method for manufacturing the compound according to any of (1) to (5), comprising a first chromatography step in which a fraction is collected by eluting an aqueous solution of a honey derived from nectar collected from manuka or manuka relative with a mixture of water and a lower alcohol.

(11) The manufacturing method according to (10), wherein the first chromatography step uses a solid phase consisting of a styrene-divinyl benzene resin material.

(12) The manufacturing method according to (10) or (11), wherein the first chromatography step is a chromatography step using a mobile phase having a water-lower alcohol gradient composition and a stepwise composition.

(13) The manufacturing method according to any of (1) to (12), further comprising a second chromatography step in which the fraction is eluted with an acidic mobile phase, and the resulting fraction is collected.

(14) The manufacturing method according to any of (10) to (13), wherein the second chromatography step is a reversed-phase liquid chromatography step.

(15) The manufacturing method according to any of (10) to (14), further comprising: prior to the first chromatography step, a step of separating a more hydrophilic first fraction and a more hydrophobic second fraction containing the compound from the aqueous solution of honey derived from nectar collected from manuka or a manuka relative, and a step of separating a more hydrophobic third fraction containing methyl syringate and a more hydrophilic fourth fraction containing the compound from the second fraction.

(16) A processing method for obtaining the compound according to any of (1) to (5) from honey from honey derived from nectar collected from manuka or a manuka relative, the method comprising:

a step of separating a more hydrophilic first fraction and a more hydrophobic second fraction containing the compound from the aqueous solution of honey derived from nectar collected from manuka or a manuka relative; and a step of separating a more hydrophobic third fraction containing methyl syringate and a more hydrophilic fourth fraction containing the compound from the second fraction.

(17) A method of measuring the compound according to any of (1) to (5) in honey, comprising a chromatography step in which an aqueous solution of honey is eluted with an acidic mobile phase, and the resulting fraction is collected.

(18) A honey evaluation method, comprising a step of measuring an amount of the compound according to any of (1) to (5) in honey.

(19) The evaluation method according to (18), further comprising a step of measuring an amount of methyl syringate in honey.

(20) The evaluation method according to (18) or (19), wherein an effect selected from antibacterial activity and anti-inflammatory activity is evaluated in honey.

DESCRIPTION OF EMBODIMENTS

The disclosures of the Description relate to a novel glycoside compound associated with anti-inflammatory activity and the like in manuka honey, and to a use therefor. The novel glycoside of the invention (hereunder called simply the novel glycoside) has MPO inhibition activity. Like the novel glycoside, the MSYR contained in manuka honey also has MPO inhibition activity, and the novel glycoside or the novel glycoside and MSYR may be used as MPO activity inhibitors.

The amount of the novel glycoside in manuka honey correlates with UMF, which is used as an index of the antibacterial activity of manuka honey, and is useful as an evaluation marker for manuka honey and other honeys. Moreover, the novel glycoside can be assayed easily and in a short amount of time by liquid chromatography or the like. Thus, an evaluation equivalent to UMF evaluation can be accomplished without the complex and time-consuming measurements of antibacterial activity required in the past.

It was also discovered for the first time that the amount of MSYR having MPO inhibition activity in manuka honey is inversely correlation with UMF. Like the novel glycoside, MSYR can be easily extracted and measured, so MSYR can also be used to evaluate manuka honey.

The novel glycoside not only has excellent MPO inhibition activity, but is also a marker for bioactivity in manuka honey. Moreover, the novel glycoside can be easily and rapidly measured in honey. Therefore, the novel glycoside may be used to advantage as a marker that allows easy and rapid evaluation of the bioactivity of manuka honey and other honeys. This novel glycoside is superior to MGO, another marker compound contained in manuka honey. This is because MGO requires complex operations, such as conversion to a derivative prior to HPLC measurement.

Embodiments of the disclosures of the Description are explained in detail below.

(Novel Glycoside)

The novel glycoside is represented by the following formula.

[C3]

As shown in the formula above, the novel glycoside is a glycoside obtained by glycosidation of an MSYR derivative with 2 to 4 glucose molecules. This compound is a novel compound that the inventors discovered by focusing on the anti-inflammatory activity of manuka honey and screening for compounds having MPO inhibition activity.

The novel glycoside includes a compound in which $R_1$, $R_2$ and $R_3$ in the formula above each independently represent hydrogen atoms or optionally substituted $C_{1-4}$ alkyl groups. The $C_{1-4}$ alkyl groups may be linear or branched. More specific examples include methyl, ethyl, n-propyl, isopropyl, n-butyl, sec-butyl and tert-butyl groups. 1 or 2 or more hydrogen atoms may be substituted in these alkyl groups. Examples of substituents include hydroxyl groups, halogen atoms, hydroxyalkyl groups and the like. In the novel glycoside, $R_1$, $R_2$ and $R_3$ are preferably all methyl groups.

The novel glycoside includes a compound in which m in the formula above is an integer from 1 to 3. Giving m a value of 1 produces a glycoside (MGGD) with two glycosylated glucose derivatives, while giving m a value of 2 produces a glycoside with three glycosylated glucose derivatives, and giving m a value of 4 produces a glycoside with four glycosylated glucose derivatives. The inventors simultaneously screened manuka honey for glycosides comprising MSYR with 3 or 4 glycosylated molecules of glucose.

The novel glycoside encompasses a compound in which $R_{4-m}$, $R_{5-m}$ and $R_{6-m}$ in the formula above each independently represent hydrogen atoms or optionally substituted $C_{1-4}$ alkyl groups. The $C_{1-4}$ alkyl groups are defined in the same way as the alkyl groups of $R_1$, $R_2$ and $R_3$. The substituents are also defined in the same way as the substituents of the alkyl groups in $R_1$, $R_2$ and $R_3$.

When m is 1 in the formula above, $R_{4-1}$, $R_{5-1}$ and $R_{6-1}$ each independently represent hydrogen atoms or optionally substituted $C_{1-4}$ alkyl groups, while when m is 2, $R_{4-1}$, $R_{5-1}$ and $R_{6-1}$ and $R_{4-2}$, $R_{5-2}$ and $R_{6-2}$ each independently represent hydrogen atoms or optionally substituted $C_{1-4}$ alkyl groups. When m is 3, $R_{4-1}$, $R_{5-1}$ and $R_{6-1}$, $R_{4-2}$, $R_{5-2}$ and $R_{6-2}$ and $R_{4-3}$, $R_{5-3}$ and $R_{6-3}$ each independently represent hydrogen atoms or optionally substituted $C_{1-4}$ alkyl groups.

In the novel glycoside, hydrogen atoms preferably dominate in $R_{4-m}$, $R_{5-m}$ and $R_{6-m}$ and more preferably all of $R_{4-m}$, $R_{5-m}$ and $R_{6-m}$ are hydrogen atoms.

The novel glycoside encompasses a compound in which $R_7$, $R_8$, $R_9$ and $R_{10}$ in the formula above are each independently a hydrogen atom or optionally substituted $C_{1-4}$ alkyl group. The $C_{1-4}$ alkyl groups are defined in the same way as the alkyl groups of $R_1$, $R_2$ and $R_3$. The substituents are also defined in the same way as the substituents of the alkyl groups in $R_1$, $R_2$ and $R_3$. In the novel glycoside, $R_7$, $R_8$, $R_9$ and $R_{10}$ are preferably all hydrogen atoms, One example of the novel glycoside is a compound represented by the following formula (in which m is an integer from 1 to 3). Typically, this is methyl-4-O-[β-D-glucopyranosyl-(1→6)-β-D-glucopyranosyl]-3,5-dimethoxybenzoate (MGGD), in which m is 1 in the formula below:

[C4]

(in which m represents an integer from 1 to 3).

(MPO Activity Inhibitor)

The MPO activity inhibitor of the invention may have the novel glycoside as an active ingredient. The novel glycoside has MPO inhibition activity. The inventors discovered MPO inhibition activity for MGGD, and considering that MSYR has MPO inhibition activity and that enzymes that cleave β-1-6 glycosidic bonds are widespread, the novel glycoside (including MGGD) appears to be a compound or a precursors of a compound having MPO inhibition activity, and all of the novel glycosides can be said to function as MPO activity inhibitors.

The MPO inhibition activity of the novel glycoside may be measured for example by the methods described in the literature (Biosci. Biotechnol. Biochem. 2003, 67(5), pp 1136-1139). That is, L-tyrosine is dissolved as a substrate in phosphate buffer (pH 7.4), enzyme myeloperoxidase is added thereto together with a candidate inhibitory compound, hydrogen peroxide is added to initiate an enzyme reaction, and after 15 minutes at 37° C. a catalase is added, and the remaining hydrogen peroxide is removed to terminate the reaction. The low-molecular-weight component alone is removed with a centrifugal ultrafiltration membrane, and fluorescence from dityrosine is detected at an excitation wavelength of 300 nm and a fluorescence wavelength of 400 nm by reversed-phase HPLC using an ODS column. MPO inhibition activity can be evaluating by measuring the increase and decrease in the peak from dityrosine.

Myeloperoxidase (MPO) is an enzyme found mainly in neutrophils, and is closely associated with biological control in bacterial infections. In the presence of hydrogen peroxide and halogens, MPO is reported to eliminate microbial invaders from the body by producing the strong active species as represented by hypochlorous acid and hypobromous acid. Associations have also been reported between MPO and atherosclerosis, lung cancer, Alzheimer's disease and multiple sclerosis. MPO is also present at sites of atherosclerosis, and is reportedly involved in the onset mechanisms of inflammation and cardiovascular disease. Thus, it is possible to infer an association between MPO inhibition activity on the one hand and anti-inflammatory action and (the prevention, treatment and the like of) various diseases including those listed above. A compound having MPO inhibition activity can be expected to have an anti-inflammatory effect.

MSYR (methyl syringate) from manuka honey has already been reported to have MPO inhibition activity. MSYR can be separated from manuka honey at the same time as MGGD. An MPO activity inhibitor containing both of these is useful.

(Honey Evaluation Marker, Kit and Honey Evaluation Method)

(Honey Evaluation Marker)

The honey evaluation marker disclosed in this Description (hereunder called simply "the marker") contains the novel glycoside. The novel glycoside correlates with UMF, a known evaluation marker for the bioactivity and the like of manuka honey. That is, manuka honey with a high UMF value also has a high value for the novel glycoside. Thus, the novel glycoside can be used as an index for UMF evaluation. According to the inventors and others, the novel glycoside is found hardly at all outside manuka honey. Apart from honeys derived from manuka (*Leptospermum scoparium*), which grows only in New Zealand, and its relative *Leptospermum polygalifolium*, [the novel glycoside] is found only in trace quantities in other New Zealand honeys. The bioactivity, quality and the like of a honey can therefore be evaluated by determining whether or not it contains the novel glycoside, and in what quantity. In addition to determining whether a honey is manuka honey, screening of new honeys containing the novel glycoside can also be implemented.

Because the novel glycoside correlates particularly with UMF, which is an index of antibacterial activity, the marker can be used to evaluate antibacterial activity. Because the novel glycoside has MPO inhibition activity, moreover, the marker can be used to evaluate the MPO inhibition activity and other anti-inflammatory activity of honey.

For the novel glycoside to be used as a marker, it is isolated from honey and identified or assayed. The isolation, identification and assaying of the novel glycoside from honey are explained below. The methods using known analysis equipment disclosed in the examples and the like can be used to identify the novel glycoside, or the novel glycoside may be prepared as a standard substance and compared by chromatography or the like. Various methods may also be applied to assaying the novel glycoside. When MSYR is used as a marker, it can also be isolated, identified and assayed in much the same way as the novel glycoside.

(Evaluation Kit)

The honey evaluation kit disclosed in this Description may contain the novel glycoside and methyl syringate. The inventors discovered that the amount of methyl syringate (MSYR) correlates inversely with the UMF of manuka honey. Thus, a more specific evaluation can be achieved by combining the novel glycoside (which correlates with UMF) with MSYR (which correlates inversely with UMF).

(Honey Evaluation Method)

The honey evaluation method disclosed in this Description may comprise a step of identifying the novel glycoside or measuring the amount of the novel glycoside in honey. This is because the novel glycoside is useful for evaluating the bioactivity of honey as discussed above. The method may also comprise a step of identifying MSYR or measuring the amount of MSYR, because this can make the evaluation more specific. The antibacterial activity, anti-inflammatory activity and other bioactivity of honey can be evaluated by this method.

(Method of Manufacturing Novel Glycoside)

The method of manufacturing the novel glycoside may comprise a first chromatography step in which a fraction is collected by eluting an aqueous solution of honey derived from nectar collected from manuka or a related plant with a mixture of water and a lower alcohol. The compound can be obtained easily by this manufacturing method.

(First Chromatography Step)

In the mixture of water and a lower alcohol, the water may also be an acidic liquid. The acid may be an inorganic or organic acid such as acetic acid, formic acid or trifluoracetic acid. The water may also contain a salt such as acid ammonium*, ammonium acetate or the like. The lower alcohol is preferably an alcohol that is compatible with water, and specifically a $C_{1-4}$ linear or branched alcohol may be used. Examples include methanol, ethanol, n-propanol, isopropanol, n-butanol, 2-butanol and tert-butanol.

The form of chromatography in the first chromatography step is not particularly limited. It is not limited to column chromatography, and may take various other forms. A carrier capable of fractionating low-molecular-weight compounds in general can be used as the separation material. Typically, a hydrophobic (reversed-phase) carrier having an aromatic and/or chain hydrocarbon structure may be used. For example, a carrier consisting of a styrene-divinylbenzene resin material may be used. The carrier may also have suitable pores. The outer shape of the carrier is not particularly limited.

The novel glycoside is contained in a fraction eluted or extracted with the mixture of water and a lower alcohol. By varying the relative proportions of the water and lower alcohol appropriately while collecting the novel glycoside, it is possible to determine the most appropriate proportions for elution or the like of the glycoside, although these differ according to the type of carrier. Separation and purification may also be performed as necessary, but partial purification is also possible since even a crude fraction is useful in some cases.

For example, using a typical hydrophobic carrier (such as a styrene-divinylbenzene resin material), if chromatography is performed by gradient elution with a mobile phase (gradient) having a temporal gradient composition of water and methanol or another lower alcohol, or by stepwise elution with a mobile phase in which the compositional ratio is varied in stages, the novel glycoside is easily fractionated in a fraction with a 7:3 to 4:6 volume ratio of the mixture of water and a lower alcohol. More specifically, the fraction has a volume ratio of 7:3 to 5:5, or even more specifically 7:3 to 6:4, or most particularly 6:4.

(Second Chromatography Step)

A second chromatography step may also be included in which this fraction is eluted with an acidic mobile phase to collect a fraction. It is thus possible to obtain the novel glycoside with greater purity. Identification and detection of the compound may be performed at the same time.

Reversed-phase liquid chromatography is preferably used for this second chromatography step. A reversed-phase carrier having alkyl groups with about 8 to 20 carbon atoms is preferably used as the carrier. The mobile phase may be set appropriately according to the carrier, but since the compound is a glycoside, a mobile phase containing water is preferable, and considering the structure of the novel glycoside, an acidic mobile phase is recommended for ease of elution. Thus, a mixture or gradient of an acidic aqueous phase and an organic phase is preferably used as the mobile phase. The aqueous phase for the mobile phase may be acidic water containing trifluoracetic acid, acetic acid, formic acid or the like. The organic phase may be acetonitrile, methanol, butanol, DMSO, DMF or the like.

Hydrophilic interaction liquid chromatography (HILIC) designed to retain a hydrophilic compound by means of hydrophilic groups held on a stationary phase may be used for the second chromatography step.

To separate out the novel glycoside, the presence of the novel glycoside in the eluted fractions is detected by a suitable detection method, the fraction containing the novel glycoside is identified, and the novel glycoside is isolated from this fraction as necessary and purified as necessary. Methods for further purification and the like of glycosides such as the novel glycoside after they have been fractionated by chromatography are well known to those skilled in the art.

The means of detecting the novel glycoside is not particularly limited. An ordinary ultraviolet absorption detector may be used, or a detection means (such as MS) suited to the structure of the novel glycoside may be used. The detection wavelength is not particularly limited, but a wavelength of 262 mm (characteristic of the novel glycoside) and neighboring wavelengths (±20~50 nm) are preferred.

The novel glycoside can be detected, identified and also assayed with great precision by the second chromatography step. Using high-performance liquid chromatography, it is possible to detect and separate out the novel glycoside and MSYR over time from the eluted fractions by a suitable detection means, and to identify and assay them using standard substances or the like.

In the method of manufacturing the novel glycoside above, MSYR is also separated out from the honey. In the first chromatography step, MSYR can be isolated at the same time as the novel glycoside, or at a higher concentration by changing the water-lower alcohol mixture so that the proportion of the lower alcohol is higher than for the novel glycoside, such as by changing the volume ratio of water to lower alcohol from 6:4 to 4:6 or thereabouts for example. MSYR can also be isolated, detected, identified and assayed even in the presence of the novel glycoside by applying the second chromatography step as for the novel glycoside. In a typical second chromatography step, MSYR is effectively isolated from the novel glycoside.

The following steps may also be adopted before applying the aqueous solution of honey in the first chromatography step. That is, it is possible to include both a first separation step of separating a hydrophilic first fraction and a hydrophobic second fraction containing the novel glycoside from an aqueous solution of honey derived from nectar collected from manuka or a related plant, and a second separation step of separating a hydrophobic third fraction containing methyl syringate and a hydrophilic fourth fraction containing the novel glycoside from the second fraction. This pre-treatment allows the process to be scaled up, and helps to improve separation and the like in the subsequent first chromatography step and second chromatography step. Moreover, the second chromatography step may then be omitted or speeded up.

In the first separation step, the water-soluble compounds and sugars in the aqueous solution of honey are separated out into the first fraction, while the novel glycoside is separated out into the second fraction. The methods in the first separation step are not particularly limited, and can be selected appropriately according to the polarity and the like of the novel glycoside and the sugars and other water-soluble compounds in the honey. For example, the following methods may be adopted.

The first separation step may be performed for example by applying the solution to the carrier used in the first chromatography step. The mode of application is not particularly limited, and may be either by column chromatography, or by mixing the carrier and the solution together in a suitable container. The novel glycoside and methyl syringate are thus partitioned onto the hydrophobic carrier (second fraction), while the more hydrophilic water-soluble compounds and sugars are partitioned into the water phase (first fraction). The water-soluble compounds and sugars can then be efficiently removed by washing and removing the water phase, while retaining the novel glycoside and methyl syringate on the carrier. Removal of the water-soluble compounds and sugars by the water phase is repeated a suitable number of times as necessary. The novel glycoside and methyl syringate can then be collected from the carrier by washing and eluting the carrier with methanol to obtain the second fraction.

In the second separation step, a more hydrophobic third fraction containing methyl syringate and a more hydrophilic fourth fraction containing the novel glycoside are separated from the second fraction. The methods in the second separation step are not particularly limited, and can be selected appropriately according to the polarity and the like of the novel glycoside and the sugars and other water-soluble compounds in the honey. For example, the following methods may be adopted.

In the second separation step, for example the methanol or other solvent is first removed by evaporation or the like from the second fraction, an MSYR-compatible solvent such as ethyl acetate that dissolves MSYR is added to the concentrated fraction together with water or another novel glycoside-compatible solvent that dissolves the novel glycoside but phase separates because it is not compatible with the MSYR-compatible solvent, and liquid-liquid partition is performed with a separation funnel. Because the novel glycoside is partitioned in the water layer (fourth fraction) while the MSYR moves to the ethyl acetate layer (third fraction), the MSYR and novel glycoside can be separated in this way.

The MSYR-compatible solvent and novel glycoside-compatible solvent may be selected appropriately from known solvents used in ordinary liquid-liquid partition, considering the solubility of the MSYR and novel glycoside, the compatibility of the solvents and the like.

These separations steps may be performed by the same kind of chromatography as in the first chromatography step, but may also be performed by a batch process in a suitable container.

After the second separation step, the MSYR from the third fraction may be further separated and purified by chromatography or the like as in the second chromatography step using a suitable hydrophobic carrier. The MSYR can thus be collected, detected, assayed and the like. After the second separation step, the novel glycoside may be further separated and purified by performing a first chromatography step and a second chromatography step as necessary. When the fourth fraction is applied to the first chromatography step, it may also be concentrated appropriately The first separation step and second separation step explained above may be performed independently as pre-processing methods for obtaining the novel glycoside and/or methyl syringate.

(Method for Measuring Novel Glycoside in Honey)

The method for measuring the novel glycoside in honey disclosed in this Description may comprise a step of collecting a fraction eluted in an acidic mobile phase by chromatography of an aqueous solution of honey. The novel glycoside can be easily separated from honey and detected and identified by this measurement method. The content of the second chromatography step for the novel glycoside may be applied as is to the collection, detection and assaying of the novel glycoside. That is, it can be detected and assayed using the detection methods applied to the fraction eluted from the acidic mobile phase.

This novel glycoside, as mentioned above, is not found in honey other than that derived from nectar collected from manuka or a related plant. Thus, it is thought that detection and assay of the novel glycoside is useful as a manuka honey marker, or in other words for verifying place of origin and mixing ratio.

EXAMPLES

The disclosures of this Description are explained in more detail below using examples, but of course these disclosures are not limited to the examples alone.

Example 1

A glycoside was purified using commercial manuka honey. 40 g of commercial manuka honey (preferably a product with a high UMF value) was added to 200 ml of water, which was warmed to dissolve the honey. A glass open column was packed with the Mitsubishi Chemical ion-exchange resin Diaion Sepabeads HP20 (using about 300 ml in a swollen state), and the dissolved manuka honey was passed through the column, followed by 500 ml of water. 500 ml each of solutions of water and methanol in ratios of 8/2, 6/4, 4/6 and 2/8 and a solution of methanol alone were passed through the column, and only the 6/4 and 4/6 water/methanol solutions were collected and concentrated with a rotary evaporator, dissolved again in a small amount of water/methanol mixture, and separated and purified under HPLC conditions.

HPLC Separation Conditions
Column: Combi-RP (20×100 mm)
Flow rate: 5 ml/min
Elution solvent: 0.1% acetic acid/acetonitrile=85/15
Detection wavelength: 262 nm The resulting purified substance was concentrated, and MGGD was confirmed using various kinds of machine analysis. 30 mg was obtained from 63.5 g (wet weight) of manuka honey, for a yield of 0.047%.

Figure 1:
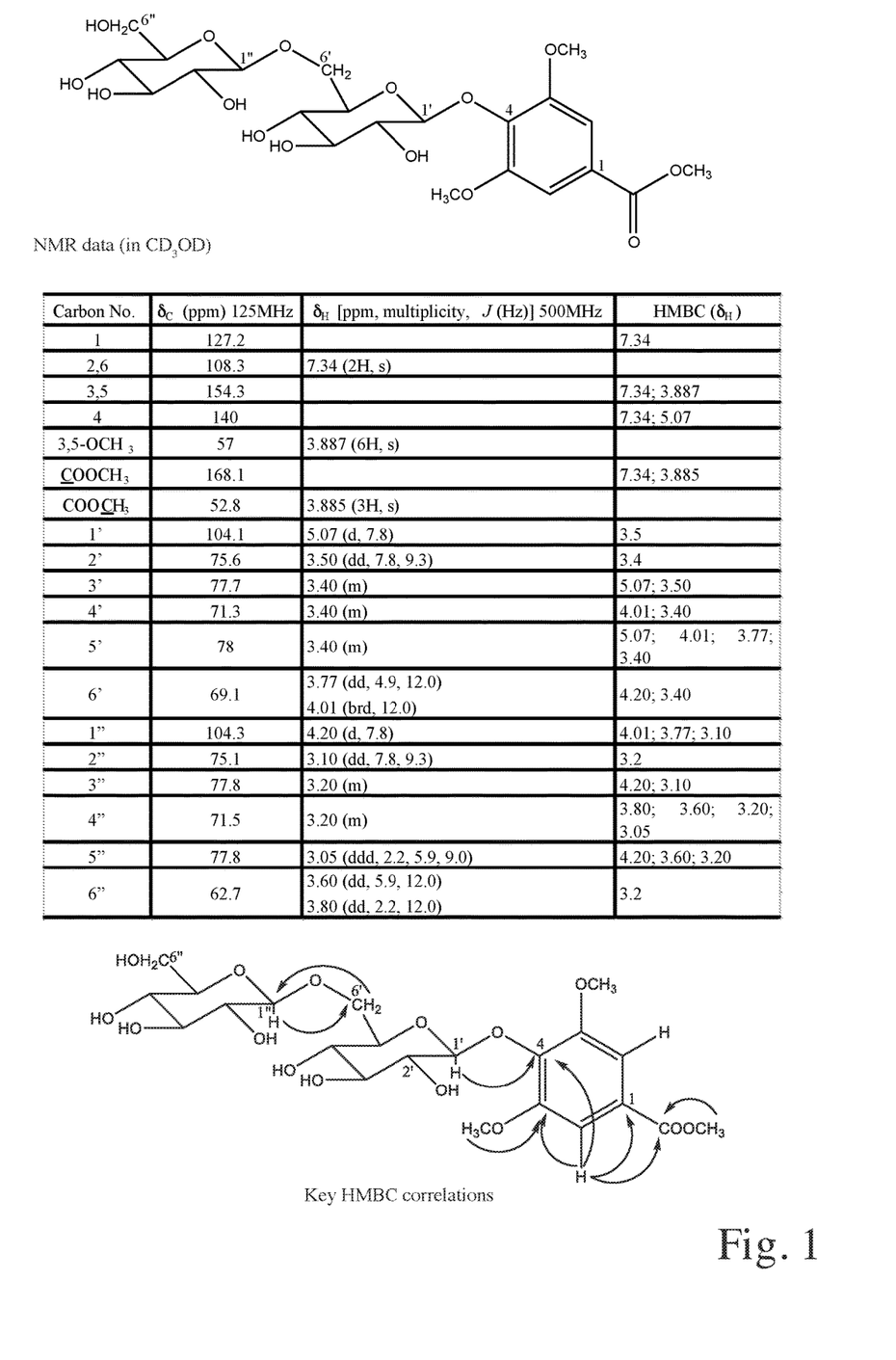
FIG. 1 shows the Key HMBC correlations from NMR (HMBC) correlation spectroscopy of the glycoside MGGD.
Figure 2:
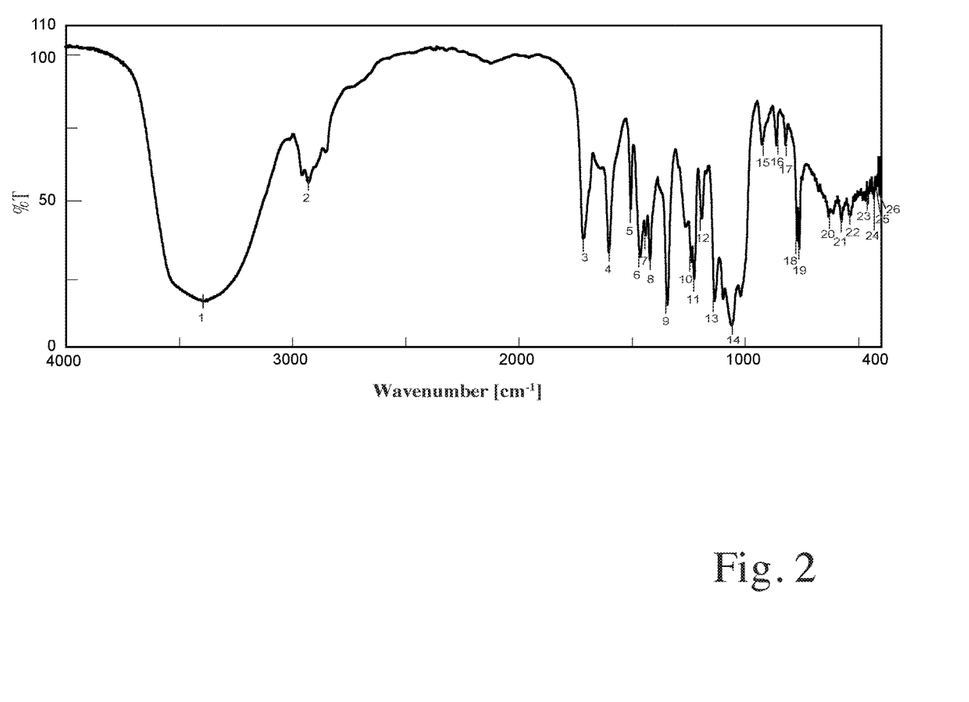
FIG. 2 is an infrared spectrum FT-IR chart of the glycoside MGGD.
Figure 3:
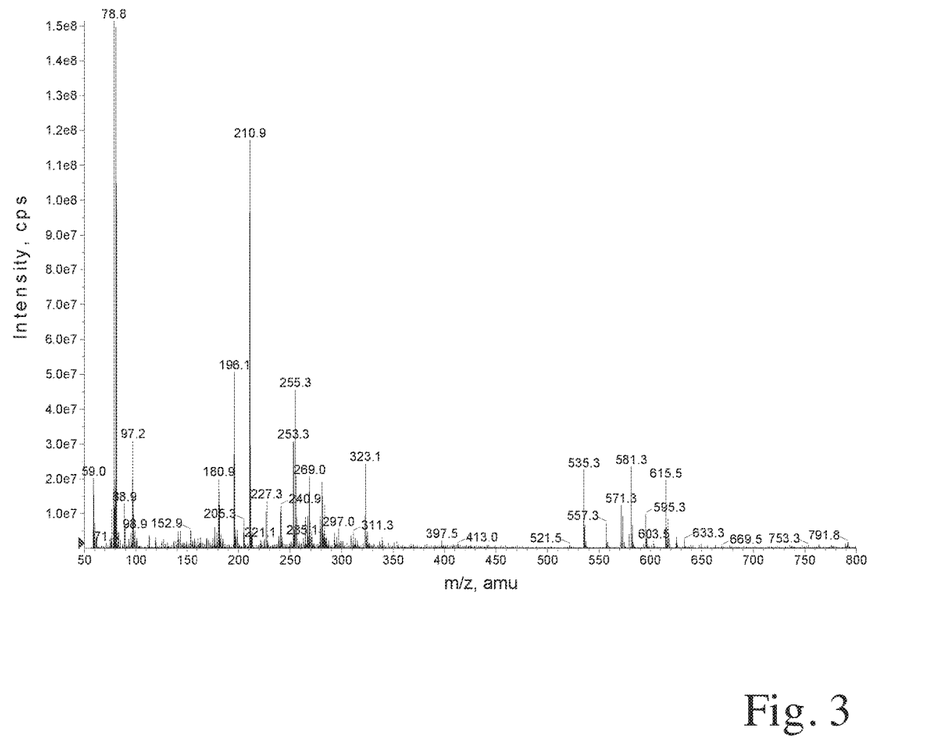
FIG. 3 is a mass spectrometry (MS) chart obtained by Q1 mass scanning of the glycoside MGGD.
Figure 4:
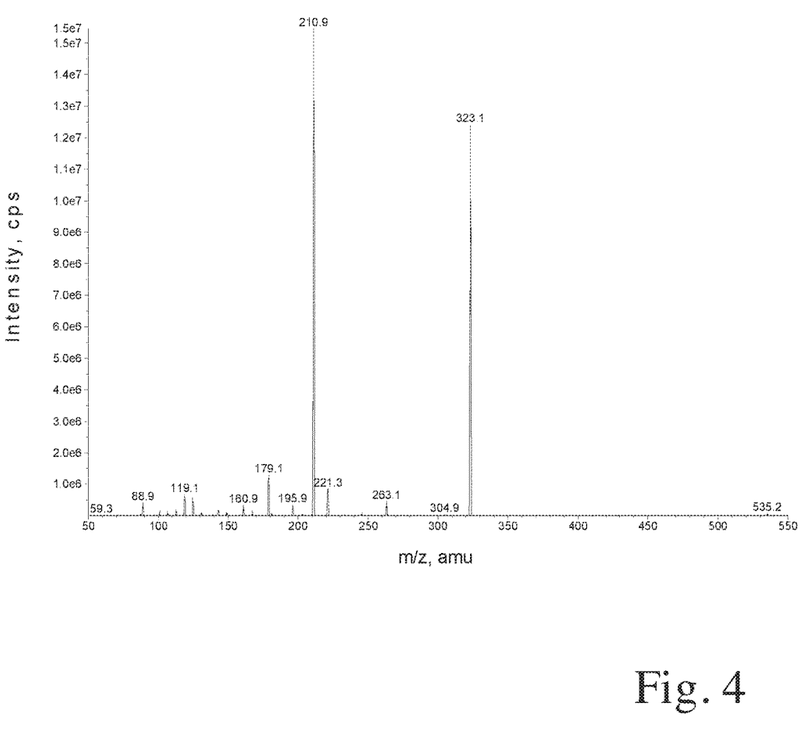
FIG. 4 is a mass spectrometry (MS) chart obtained by product scanning of the glycoside MGGD.

The NMR results are shown in FIG. 1. The FTIR results are shown in FIG. 2, and the mass spectroscopy results are shown in FIG. 3 and FIG. 4. In addition, the physical values for the resulting substance were as follows.

$[\alpha]D=-30.1$ (c=0.69, MeOH)
ESI-MS m/z 535 [M-H]-, molecular weight 536
$\lambda$ max
262 nm From the results in FIGS. 1 to 4, the resulting compound was specified as methyl 4-O[β-D-glucopyranosyl-(1→6)-β-D-glucopyranosyl]-3,5-dimethoxybenzoate (MGGD).

Example 2

Using the novel glycoside MGGD obtained in Example 1 and commercial MSYR as reference standards, the two compounds were assayed in manuka honey. They were also assayed in the same way in asphodel honey (from Sardinia, Italy), which has been reported to contain large quantities of MSYR (Non Patent Literature 4). The amounts of MGGD and MSYR were also assayed in multiple manuka honeys with different UMF values. Specifically, this was done as follows.

Figure 5:
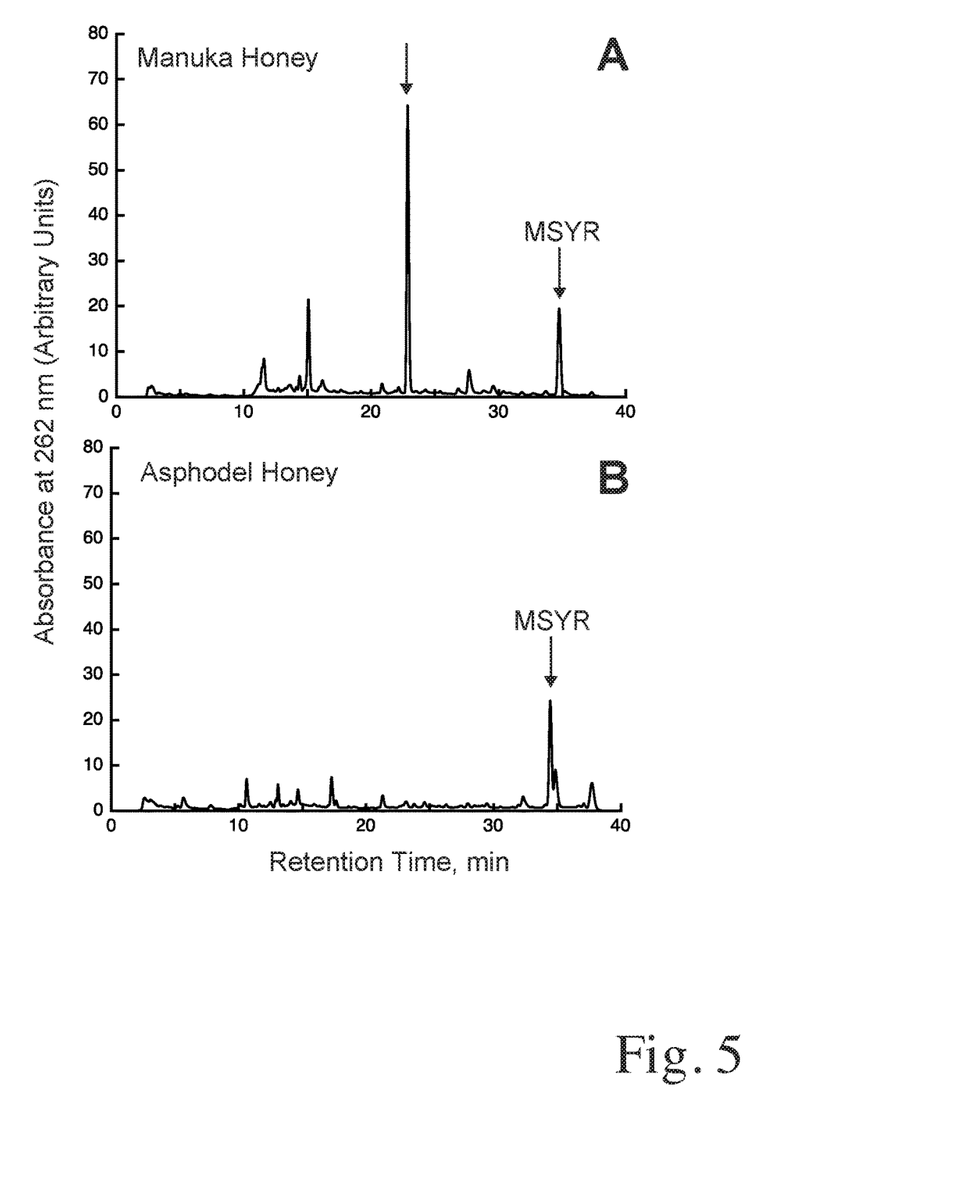
FIG. 5 is a high-performance liquid chromatography analysis graph of manuka honey.
Figure 6:
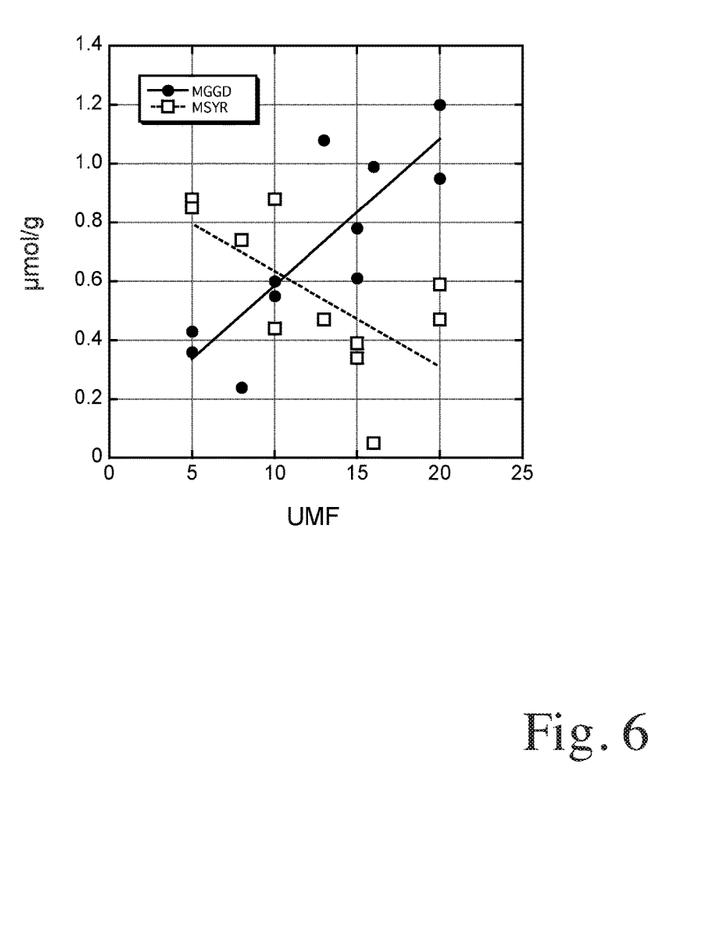
FIG. 6 shows UMF values correlated with amounts of methyl syringate (MSYR) and the glycoside MGGD (with molar amounts per gram of honey shown on the vertical axis) Asphodel honey high-performance liquid chromatography analysis graph (methyl syringate MSYR)

The honey is weighed and dissolved in water (about 100 mg/ml), and part (about 5 μl) is injected into an HPLC system equipped with a UV absorption detector (UV detector). The results are shown in FIG. 5 and FIG. 6.

HPLC Analysis Conditions
Column: Develosil ODS-HG-5 (4.6×150 mm)
Flow rate: 0.8 ml/min
Elution solvent: A: 0.1% acetic acid, B: acetonitrile
Detection wavelength: 262 nm
(Gradient Conditions)

TABLE 1

| Time, min | A solvent % |
|---|---|
| 0 | 100 |
| 30 | 70 |
| 35 | 100 |
| 50 | 100 |

The chromatogram at the top of FIG. 5 shows the results for manuka honey. As shown in this figure, MGGD and MSYR were clearly isolated by chromatography. The chromatogram at the bottom of FIG. 5 shows the results for asphodel honey. Because the novel glycoside MGGD has MSYR in its basic framework, this shows that asphodel honey, which contains large quantities of MSYR, contains no MGGD at all. Thus, it appears that MGGD is highly specific to manuka honey, and is closely associated with its bioactivity. It also shows that just because a honey contains large quantities of MSYR does not necessarily mean that it also contains MGGD.

FIG. 6 shows the results for measurement of MGGD and MSYR in manuka honeys with different UMF values. As shown in FIG. 6, there is a strong correlation between MGGD content and UMF value. However, MSYR content is inversely correlated with UMF value.

Example 3

Figure 7:
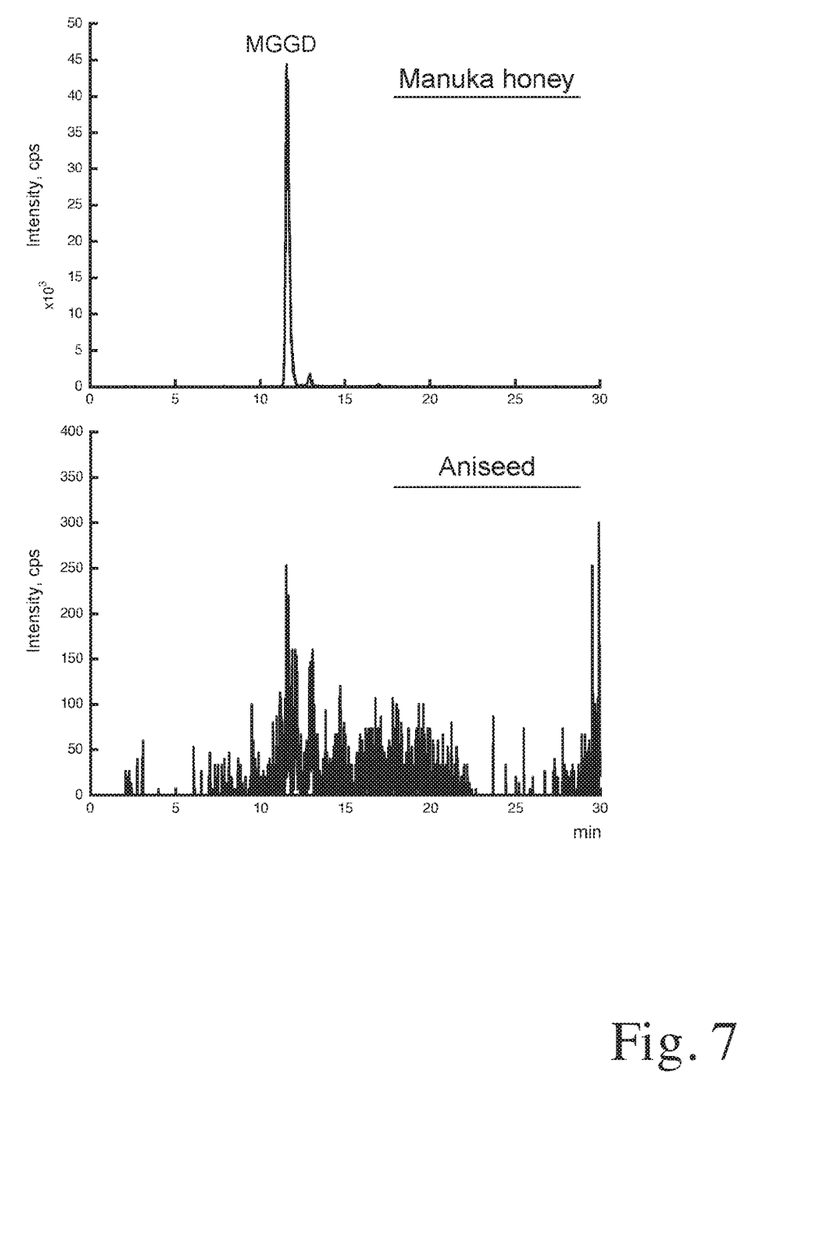
FIG. 7 shows detection results for the glycoside MGGD in manuka honey and aniseed (LC/MS/MS mass spectrograph)
Figure 8:
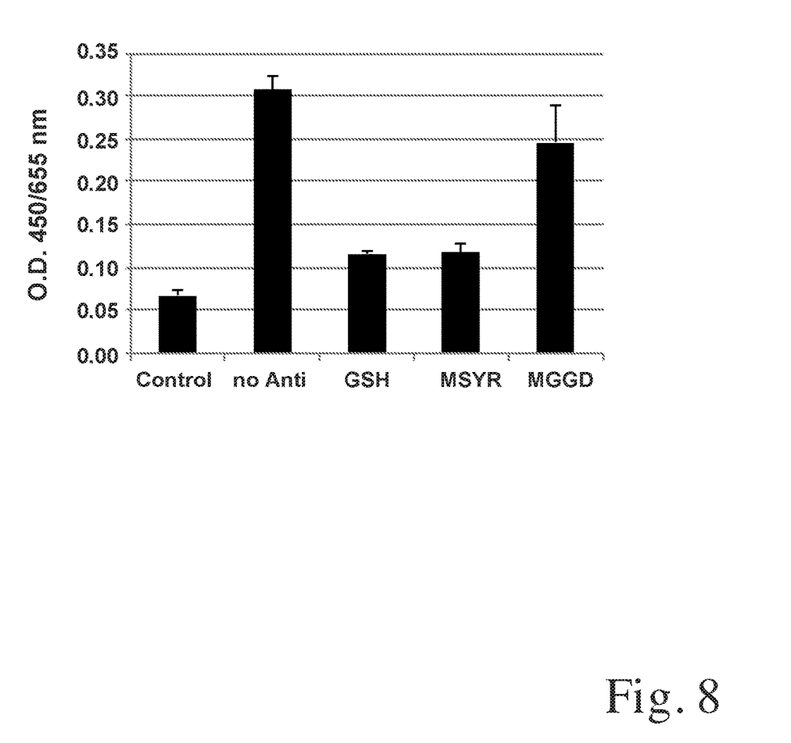
FIG. 8 shows the results of evaluation of the MPO inhibition activity of MGGD.

MGGD comprises the disaccharide gentiobiose bound to MSYR, and MSYR with a monosaccharide bound thereto has been reported in aniseed (*Aromatic compound glucosides, alkyl glucoside and glucide from the fruit of anise*. Fujimatu E, Ishikawa T, Kitajima J. *Phytochemistry*. 2003, 63(5): 609-616.). Thus, it is possible that aniseed also contains MGGD. Therefore, MGGD was measured in manuka honey and aniseed using an LC/MS/MS mass spectrograph. The analysis conditions were as follows. The results are shown in FIG. 7.

(LC/MS/MS Analysis Conditions)
Mass spectrograph: API3000
Column: Develosil ODS-HG-5 (2×150 nm)
Flow rate: 0.2 ml/min
Elution solvent: A: 0.1% acetic acid, B: acetonitrile
Injection: 5 µl
Mode: Negative electrospray ionization, Multiple Reaction Monitoring 535.1/211.1
(Gradient Conditions)

TABLE 2

| Time, min | A solvent % |
|---|---|
| 0 | 100 |
| 18 | 70 |
| 18.4 | 100 |
| 30 | 100 |

As shown in FIG. 7, MGGD was detected in manuka honey by highly sensitive analysis using an LC/MS/MS mass spectrograph, but none was detected in aniseed. This shows that MGGD is highly specific to manuka honey, and is closely associated with its bioactivity. It also shows that just because a honey contains large quantities of MSYR does not necessarily mean that it also contains MGGD.

In LC/MS analysis of manuka honey, peaks were confirmed at molecular weights of 697.2 and 859.2, corresponding, respectively, to a triglycoside and tetraglycoside of MSYR. This shows that in addition to the diglycoside MGGD of MSYR, manuka honey also contains its triglycoside and tetraglycoside. Further investigation of other manuka honeys revealed that the triglycoside and tetraglycoside were present in smaller amounts than the diglycoside, and were absent or not detected in some of the other manuka honeys.

Example 4

The MPO inhibition activities of the isolated MGGD and its aglycon MSYR were measured by evaluating inhibition of the halogenation of the tyrosine residues of a biotin-labeled protein (bovine serum albumin). It is thus possible to measure either inhibition of the MPO enzyme itself or the ability to extinguish or capture hypobromous acid (HOBr) and other active species produced by the enzyme.

The necessary solutions and the like for the reaction were prepared as follows.

(1) 0.5 µM human MPO.
(2) Xanthine oxidase (XOD) (Sigma X4500-25UN) diluted 100× with water.
(3) 5.61 µl of acetaldehyde (ALD) (Merck A4907704746) diluted in 1 ml of water to 100 mM.
(4) Biotin-BSA (Sigma-A6043-10MG) dissolved to 1 mg/ml in 0.1 M phosphate buffer with 200 µM NaBr and 200 mM NaCl added in advance, then freeze dried for storage, and diluted to 0.4 mg/ml before use.
(5) Sample prepared to 5 mM.
(6) Reduced glutathione (GSH) (Sigma G-6529) as a positive control.
(7) L-methionine, dissolved in water to 10 mM.

50 µl of Biotin-BSA and 10 µl each of the sample, MPO and XOD were added to an Eppendorf tube, water was added to a total of 100 µl, and 10 µl of ALD was added to initiate the reaction. A mixture without an added sample was prepared as a control, and a reaction initiated in the same way. After 30 minutes of reaction at 37° C., 75 µl of the reaction solution was added to a micro-spin column (Bio-Rad), and centrifuged for 4 minutes at 1000 g to collect the Biotin-BSA, while 75 µl of L-methionine was added to the supernatant to terminate the reaction.

50 µl of a 10 µg/ml concentration 3A5 antibody (Nikken Seil) recognizing dihalogenated tyrosines was coated as a primary antibody on each microplate, and left standing overnight at 4° C. This was washed three times with PBS containing 0.05% Tween20 (TPBS), and blocked with 200 µl of 1% aqueous solution of skim milk (Block Ace powder, Yukijirushi) dissolved in water. After standing for 30 minutes at 37° C. this was washed, the sample (collected Biotin-BSA) was diluted 5 times with TPBS, and 100 µl was added and left standing for 45 minutes at 37° C. This was then washed, and 100 µl of Streptavidin-Ultrasensitive, Polymer (HRP) (Sigma) diluted 7500 times in TPBS was added as a secondary antibody. This was then left standing again for 45 minutes at 37° C. and washed, after which 100 µl of a TMB (3,3'-5,5'-tetramethylbentidine) coloring reagent (A liquid/B liquid=1/1) was added, and absorbancy was measured at 450 nm/550 nm for about 10 minutes with a microplate reader. The results are shown in FIG. 9.

Figure 9:
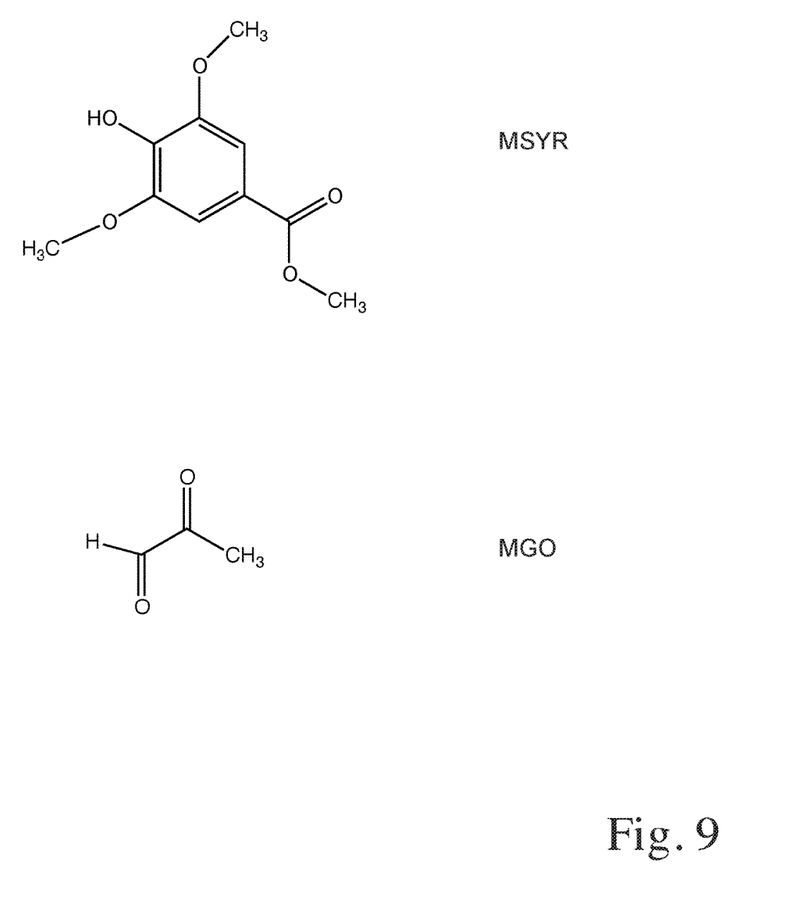
FIG. 9 shows the structures of methylglyoxal and methyl syringate.

As shown in FIG. 9, MGGD exhibited MPO enzyme inhibition activity in comparison with the coloration (halogenated tyrosine production) of the control (no Anti) with no added antioxidant.

Example 5

In this example, MSYR and MGGD were purified from commercial manuka honey. First, 500 ml of water was added to 500 g of commercial manuka honey, and shaken well to obtain a honey solution that was then mixed well with 400 ml of the HP20 resin used in Example 1 (swollen with water), and washed thoroughly with water in a Buchner funnel. Methanol was then supplied to the HP20 resin in the Buchner funnel, and a methanol eluate was collected. The methanol eluate was dried. The dried product was dissolved in 50 ml of water and transferred to a liquid separation funnel, ethyl acetate and water were added to the separation funnel and mixed to obtain 100 ml of a 1:1 (volume ratio) ethyl acetate/water mixture in the separation funnel, the ethyl acetate layer was discarded, and the steps of adding a further 50 ml of ethyl acetate, mixing well and discarding the ethyl acetate layer were repeated twice. Good distribution of MSYR in the ethyl acetate layer was confirmed by chromatography. Distribution of MGGD in the water layer was also confirmed. The HPLC conditions were as follows.
(HPLC Analysis Conditions)
Column: Chromolith HR (4.6×100 mm)
Flow rate: 1.0 ml/min
Elution solvent: A: 0.1% formic acid, B: acetonitrile
Detection wavelength: 262 nm
Program: 0 min, A90%, 10 min, A70%, 11 min, A90%, 20 min, A90%

Next, the water layer in the separation funnel was concentrated with a centrifugal evaporator, applied to an open column packed with HP20 resin and washed with water and a water:methanol mixture (8:2), after which the MGGD was eluted with a water:methanol mixture (1:1), and partition of the MGGD in the collected liquid was confirmed by chromatography. The HPLC conditions were as follows.
(HPLC Analysis Conditions)
Column: Chromolith HR (4.6×100 mm)
Flow rate: 1.0 ml/min
Elution solvent: 0.1% formic acid:acetonitrile (7:3)
Detection wavelength: 262 nm

The invention claimed is:

1. A compound represented by the following formula:

where m is an integer from 1 to 3.

2. A composition, comprising the compound according to claim 1 as an active ingredient.

3. The composition according to claim 2, further comprising methyl syringate.

4. A kit, comprising the compound according to claim 1.

5. A kit, comprising the compound according to claim 1 and methyl syringate.

6. A method for obtaining the compound according to claim 1, comprising:
preparing an aqueous solution of honey derived from nectar collected from manuka or a manuka relative; and
performing a first chromatography step comprising:
passing the aqueous solution of the honey through a solid phase consisting of a styrene-divinyl benzene resin material; and
eluting the solid phase with a mixture of water and a $C_{1-4}$ linear or branched alcohol to obtain a fraction containing the compound.

7. The method according to claim 6, wherein the eluting the solid phase with a mixture of water and a $C_{1-4}$ linear or branched alcohol comprises gradient or stepwise elution with a mobile phase in which a compositional ratio of the water to the $C_{1-4}$ linear or branched alcohol is varied in stages.

8. The method according to claim 6, further comprising performing a second chromatography step after the first chromatography step, the second chromatography step comprising:
performing reversed-phase liquid chromatography on the fraction containing the compound collected in the first chromatography step by:
passing the fraction containing the compound through a reversed-phase carrier having alkyl groups with about 8 to 20 carbon atoms,
eluting the reversed-phase carrier with an acidic mobile phase, and
collecting a resulting fraction containing the compound.

9. A processing method for obtaining the compound according to claim 1, the method comprising:
preparing an aqueous solution of honey derived from nectar collected from manuka or a manuka relative;
performing a first separation step comprising:
passing the aqueous solution of the honey through a solid phase consisting of a styrene-divinyl benzene resin material;
rinsing the solid phase with water to obtain a first fraction comprising water, and water soluble sugars and other water soluble compounds from the honey; and then
eluting the solid phase with methanol to obtain a second fraction comprising methanol, the compound, and methyl syringate; and then
performing a second separation step comprising:
evaporating the methanol from the second fraction to obtain a concentrated second fraction;
adding ethyl acetate and water to the concentrated second fraction, and allowing the ethyl acetate to phase separate from the water to obtain an ethyl acetate phase in which is dissolved the methyl syringate and a water phase in which is dissolved the compound; and
separating the ethyl acetate phase from the water phase to obtain a third fraction that contains the ethyl acetate phase and a fourth fraction that contains the water phase.

10. The method according to claim 9, further comprising:
performing a first chromatography step comprising:
passing the fourth fraction through a solid phase consisting of a styrene-divinyl benzene resin material; and
eluting the solid phase with a mixture of water and a $C_{1-4}$ linear or branched alcohol to obtain a fraction containing the compound.

11. A method of measuring an amount of the compound according to claim 1 in a sample of honey, comprising:
performing a chromatography step in which an aqueous solution of the honey is eluted with an acidic mobile phase,
collecting a resulting fraction, and
measuring the amount of the compound contained in the resulting fraction by application of a UV absorber detector or a mass spectrometer.

* * * * *